United States Patent [19]
Hale et al.

[11] Patent Number: 5,637,795
[45] Date of Patent: Jun. 10, 1997

[54] APPARATUS AND TEST METHODOLOGY FOR MEASUREMENT OF BIT/STABILIZER BALLING PHENOMENON IN THE LABORATORY

[75] Inventors: Arthur H. Hale, Houston, Tex.; Peringandoor R. Hariharan, Berkeley, Calif.; Sanjit Roy, Notre Dame, Ind.

[73] Assignee: Shell Oil Company, Houston, Tex.

[21] Appl. No.: 551,598

[22] Filed: Nov. 1, 1995

[51] Int. Cl.$^6$ .................. G06F 19/00; E21B 17/00; E21B 49/10; G01N 11/10
[52] U.S. Cl. .................. 73/152.01; 73/53.05; 73/61.62; 73/865.6; 166/250.01; 175/40
[58] Field of Search .................. 73/151, 151.5, 73/53.05, 61.41, 61.62, 865.6; 175/40; 166/250

[56] References Cited

U.S. PATENT DOCUMENTS

| | | | |
|---|---|---|---|
| 4,458,528 | 7/1984 | Roper et al. | 73/151 |
| 4,528,842 | 7/1985 | Brown | 73/61.4 |
| 4,548,080 | 10/1985 | Sweet | 73/432 SD |
| 4,760,735 | 8/1988 | Sheppard et al. | 73/151 |
| 4,829,816 | 5/1989 | Hubbard | 73/151 |
| 5,052,219 | 10/1991 | Fery et al. | 73/153 |
| 5,057,234 | 10/1991 | Bland et al. | 252/8.51 |
| 5,309,761 | 5/1994 | Ravi et al. | 73/151 |
| 5,330,016 | 7/1994 | Paske et al. | 175/320 |
| 5,361,631 | 11/1994 | Covington et al. | 73/151 |
| 5,508,915 | 4/1996 | Tsao et al. | 364/422 |

*Primary Examiner*—Hezron E. Williams
*Assistant Examiner*—J. David Wiggins

[57] ABSTRACT

A novel process and apparatus have been contrived for the study of the bit/stabilizer balling phenomenon in the laboratory. The device permits a standard testing procedure using a specially designed bob simulating the drill bit for comparing degrees of balling for different rock formations under different drilling conditions involving variable and controlled parameters like weight-on-bit, revolutions-per-minute (rpm), drilling fluids, etc.

2 Claims, 5 Drawing Sheets

FIG. 3
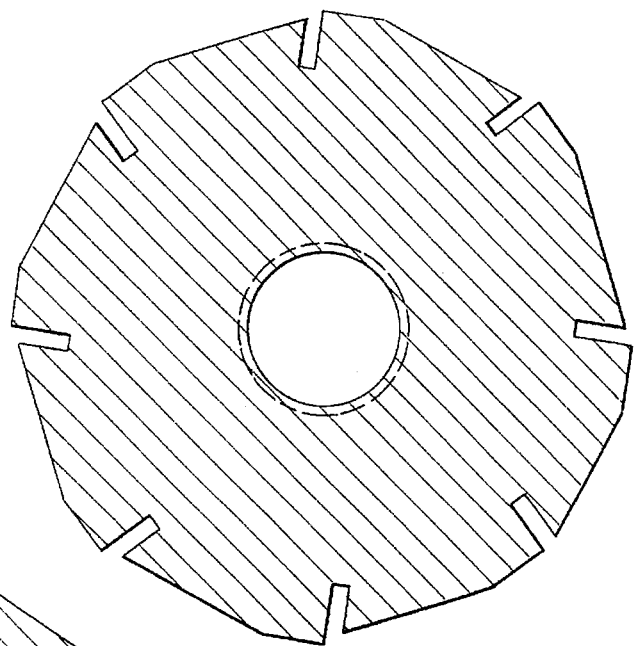
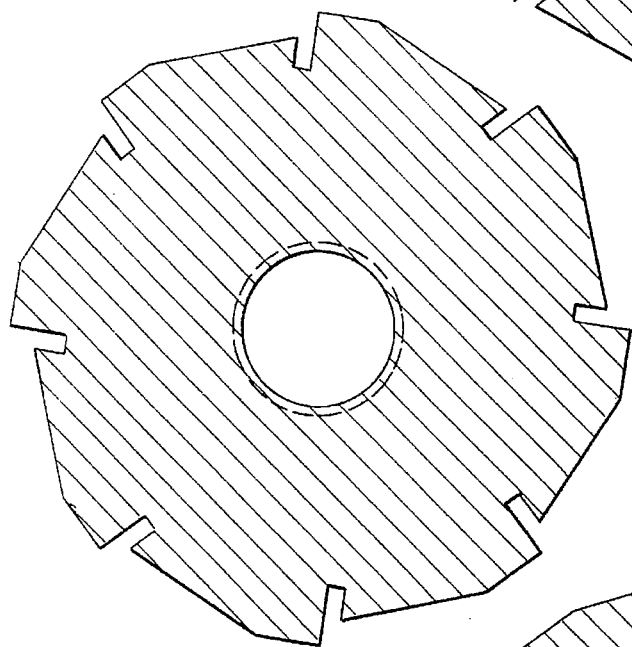
FIG. 4
FIG. 5
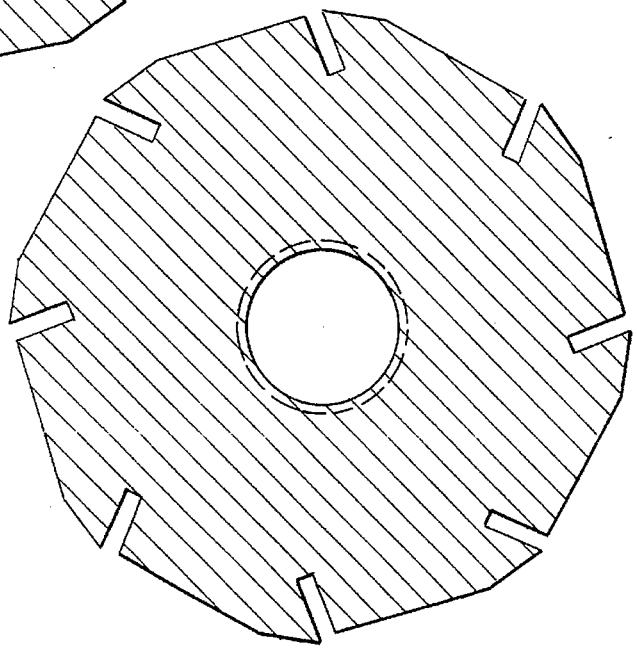

APPARATUS AND TEST METHODOLOGY FOR MEASUREMENT OF BIT/STABILIZER BALLING PHENOMENON IN THE LABORATORY

BACKGROUND OF THE INVENTION

Bit and/or stabilizer balling is regarded as a prime technical problem area in oil and gas well drilling. Balling is prevalently defined as the stuck formation material consisting of the drilled materials, also called 'drilled cuttings', or debris that is stuck tight to the surface of the bit and/or stabilizers that are otherwise hard to be removed by the hydraulic circulation of the drilling fluid present. Balling results in detrimental effects to the drilling operations in the form of decreased rate-of-penetration (ROP), frequent trips in and out of the hole causing increased cost of the drilling operation, surge and swab pressure increases, reduced weight-on-bit (WOB) and bore-hole instability.

The causes of bit-balling have been documented in the literature as being manifold. Causes vary from the type of formation that is being drilled, the design characteristics of the drill-bit, the applied down-hole hydraulics, itself consisting of the flow-rate, bit-hydraulic-horsepower (BHHP), formation confining and/or differential pressure, physical and chemical properties of the drilling fluid. However, studying the problem of bit/stabilizer balling in the field can be extremely time consuming as well as expensive. Further, it becomes a great problem to isolate and study the effects of each affecting parameters independently. Hence what is needed in the art is a new technique to study the problem of bit/stabilizer balling, the test procedure of which is quick and the methodology of which is simple yet robust, such that the desired operating conditions can be simulated quickly, providing accurate and repeatable results.

DESCRIPTION OF THE PRIOR ART

The prior art in the study of bit/stabilizer balling has consisted mainly of full-scale laboratory experimentation and field scale drilling studies. A few drilling studies utilizing micro-bits have also been conducted.

Cheatham and Nahm (1990) conducted some of the earliest full-scale drilling experiments in the laboratory to study bit-balling. Pierre shale core samples measuring 15 inches in diameter and 3 feet in length were used under separate differential and confining pressure conditions. The influence of confining pressure on bit-balling was studied as also the effect of balling on the torque while the drilling operation was in progress. Although the study provided an insight into the mechanism of balling and documented the influence of the confining pressure on balling tendency, no attempt was made to quantify the degree of balling. Further, the study was mainly focussed on roller-cone bits and on PDC (Polycrystalline Diamond Bits) in which the balling phenomena tends to be a more serious problem.

Ledgerwood and Salisbusry, "Bit-balling and Wellbore Stability of Downhole Shales", SPE22578, (October 1991), studied the bit-balling problem in shale through micro-bit drilling experiments under atmospheric as well as pressurized conditions. The micro-bit consisted of a couple of PDC cutters attached to a shaft oriented in a fish-tail fashion. The amount of balling was classified subjectively as 'severe', 'moderate', and 'slight', presenting problems in repeatability as well as a uniform means to quantify the amount of cuttings stuck on the bit.

Hemphill and Clark (1991) conducted full-scale experiments in the laboratory to observe the effect of different drilling fluids on balling in the laboratory. They further utilized the variation of the drilling torque as an indicator of the balling phenomena, pointing out the fact that when a bit got severely balled up, the torque decreased correspondingly.

Zijsling and Illerhaus (1991) documented the field performance of the "Egg-Beater" bit designed especially for the prevention of the balling. The project necessitated testing of the product in the field under controlled conditions.

Holster and Kipp (1984) conducted full-scale drilling studies in Mancos and Pierre shales and have described the influence of hydraulics on the balling tendency. However, the conclusions drawn from this work was the fact that gumbo-type shales cannot be drilled effectively and balling cannot be prevented through hydraulics alone, especially so when PDC bits are being used.

All of the above tests involved an outlay of large amounts of time and money. Frequently, even for obtaining very few data points, tests involved the setting up of huge testing procedures and mounting large rock cores under carefully controlled environmental conditions. Frequently, even after running such large elaborate experiments, the interpretations are incomplete for want of more data which demand the need for running of many such similar experiments to even form a 'trend' of data that can be interpreted with confidence. In this manner the entire process becomes an extremely tedious and tiresome research exercise.

SUMMARY OF THE INVENTION

In response to the above need in the art, for a process that provided a reliable and consistent methodology and apparatus for obtaining repeatable results quickly in the laboratory, the present invention provides a novel process and device.

A process is formulated for determining the likelihood and/or extent of bit-balling occurring in the presence of a specified formation material through which a borehole would be drilled and a specified drilling fluid which would be used to drill the borehole by providing a sample of the specified formation material or a similar substitute material; providing a sample of a specified drilling fluid or a similar substitute fluid. Providing a bob simulating a drill-bit; enclosing the bob and the formation material with sub-merged in the drilling fluid which is caused to circulate through a pump so that the same fluid recirculates during the entire duration of the test. The bit/stabilizer balling test would involve forcing the bob (simulating the drill-bit) against the formation material at a specified load (simulating a value to proportionally correspond to the weight-on-bit (WOB) being used in the field in normal or conventional drilling operations in the oil and gas industry) and rotating the bob at a constant speed (rpm) for a specified duration of time. The apparatus is instrumented to record the rotary torque during the rotation and also to record the rotary speed.

At the end of the specified duration of time of the test, the drilling fluid is drained away and the bob is removed from the spindle and weighed from which the amount of cuttings stuck on the faces and the amount of cuttings stuck in the slots of the bob are calculated separately and recorded providing a quantitative estimate of the degree of balling through the amount of cuttings stuck to the faces as well as stuck inside the slots of the bob.

The complete apparatus comprising a bob simulating a bit; the bob comprising eight different cutting faces, one part of each of which is inclined at a specified negative rake angle (FIG. 3) forming into a slot, and the other side of which forms two faces at specially inclined relief angles (FIG. 3); the entire bob formed out of material 440C steel and subsequently heat treated to required specifications; a holder for holding the rock sample, a chamber enclosing the rock sample, holder and also the drilling fluid, a fluid inlet and a fluid outlet to the chamber for circulating a drilling fluid in contact with the bob and the rock sample, means for pumping the circulating fluid, means for rotating the bob, means for applying different loads on the rock through the bob, means for measuring and recording data like rotary torque and rotary speed, means to mount samples in thermally insulated holders with the intention of maintaining the bob at particular specified polarity well isolated from rest of the apparatus, means to maintain the bob at a particular specified polarity in such a manner so as to isolate the rock sample from rest of the apparatus, a means for weighing the bob for determining the amount of rock cuttings adhering to the faces and stuck in the slots of the bob.

DESCRIPTION OF THE DRAWINGS

FIG. 3 is the front view of the first bob known as Design 1 of the invention with the following descriptive parameters:

Rake Angle=−8.5 degrees

Relief Angle I=8.5 degrees

Relief Angle II=20.0 degrees

FIG. 4 is the front view of the second bob known as Design 2 of the invention with the following descriptive parameters:

Rake Angle=−8.5 degrees

Relief Angle I=8.5 degrees

Relief Angle II=25.0 degrees

FIG. 5 is the front view of the third bob known as Design 3 of the invention with the following descriptive parameters:

Rake Angle=21.5 degrees

Relief Angle I=8.5 degrees

Relief Angle II=20.0 degrees

Figure 6:
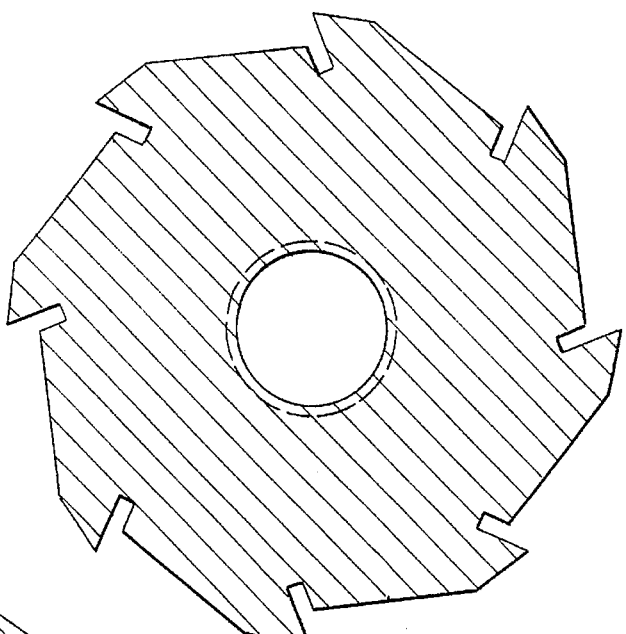

FIG. 6 is the front view of the fourth bob known as Design 4 of the invention with the following descriptive parameters:

Rake Angle=21.5 degrees

Relief Angle I=8.5 degrees

Relief Angle II=30.0 degrees

Figure 7:
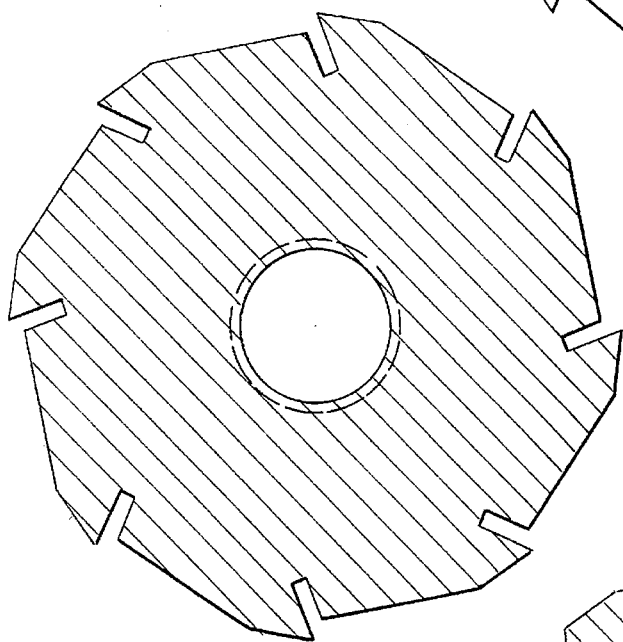

FIG. 7 is the front view of the fifth bob known as Design 5 of the invention with the following descriptive parameters:

Rake Angle=21.5 degrees

Relief Angle I=8.5 degrees

Relief Angle II=25.0 degrees

Figure 8:
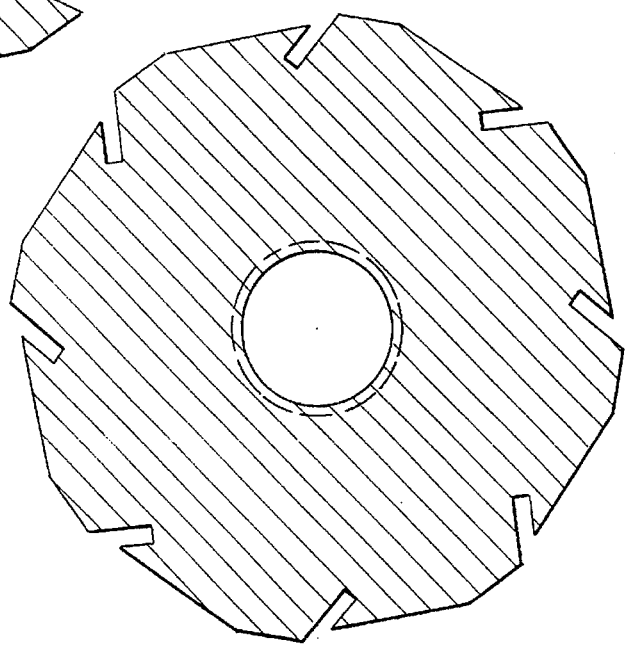

FIG. 8 is the front view of the sixth and optimized bob known as Design 6 of the invention with the following descriptive parameters:

Rake Angle=−38.5 degrees

Relief Angle I=8.5 degrees

Relief Angle II=20.0 degrees

Figure 9:
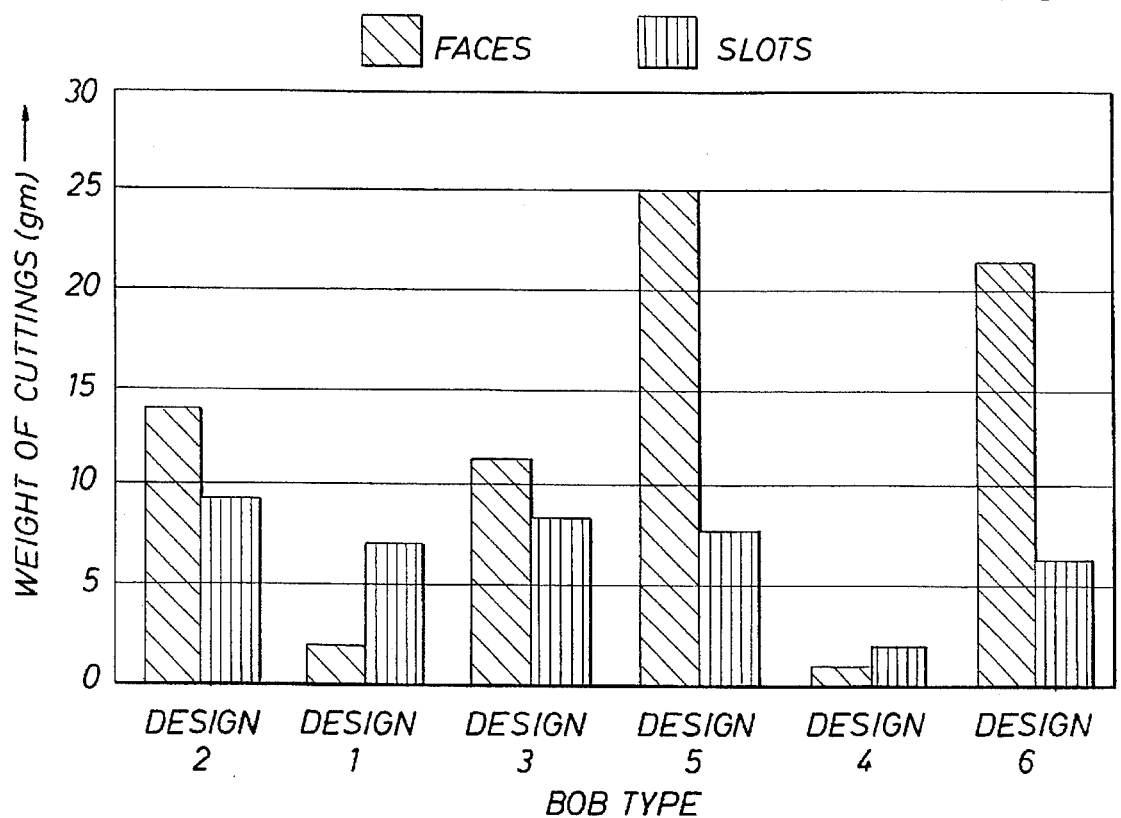

FIG. 9 provides test results showing the amount of balled-up cuttings.

Figure 10:
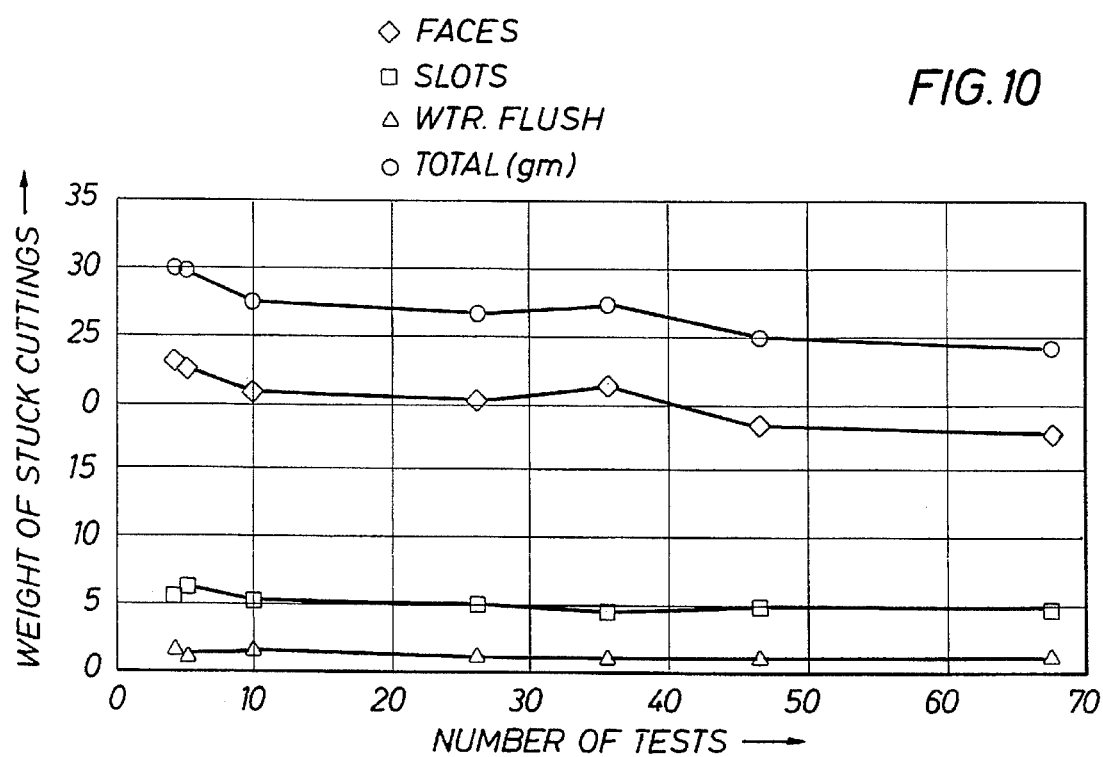

FIG. 10 shows a plot of Number of Tests versus Weight of Stuck Cuttings.

Figure 11:
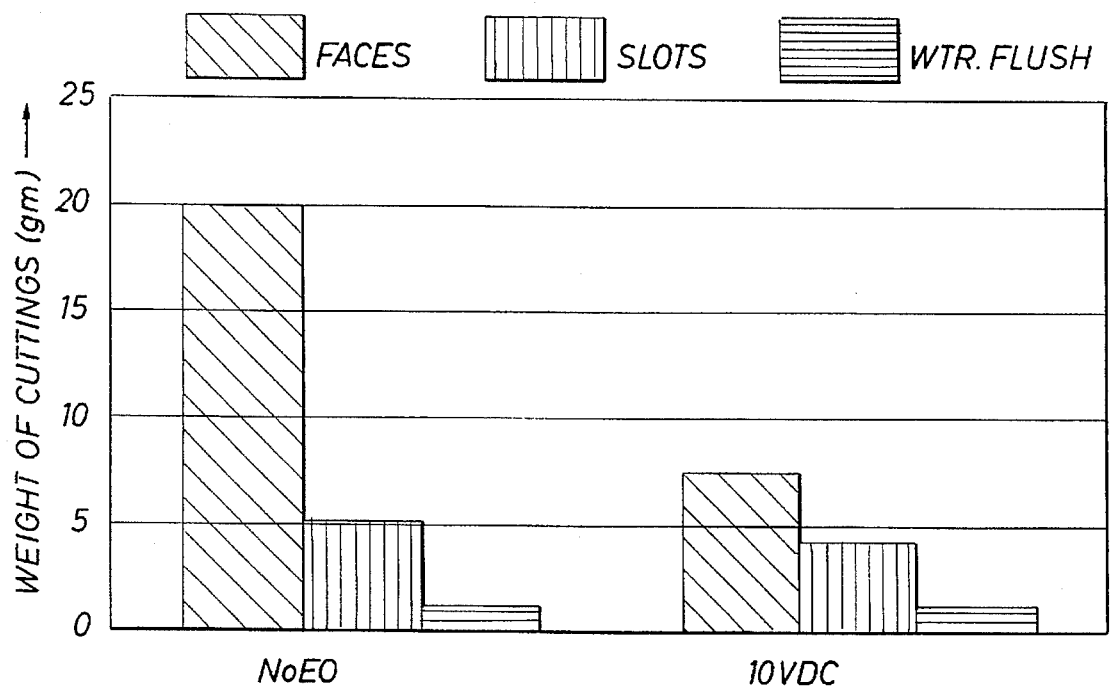

FIG. 11 shows the amount of stuck balled cuttings of Pierre II shale rock.

Figure 12:
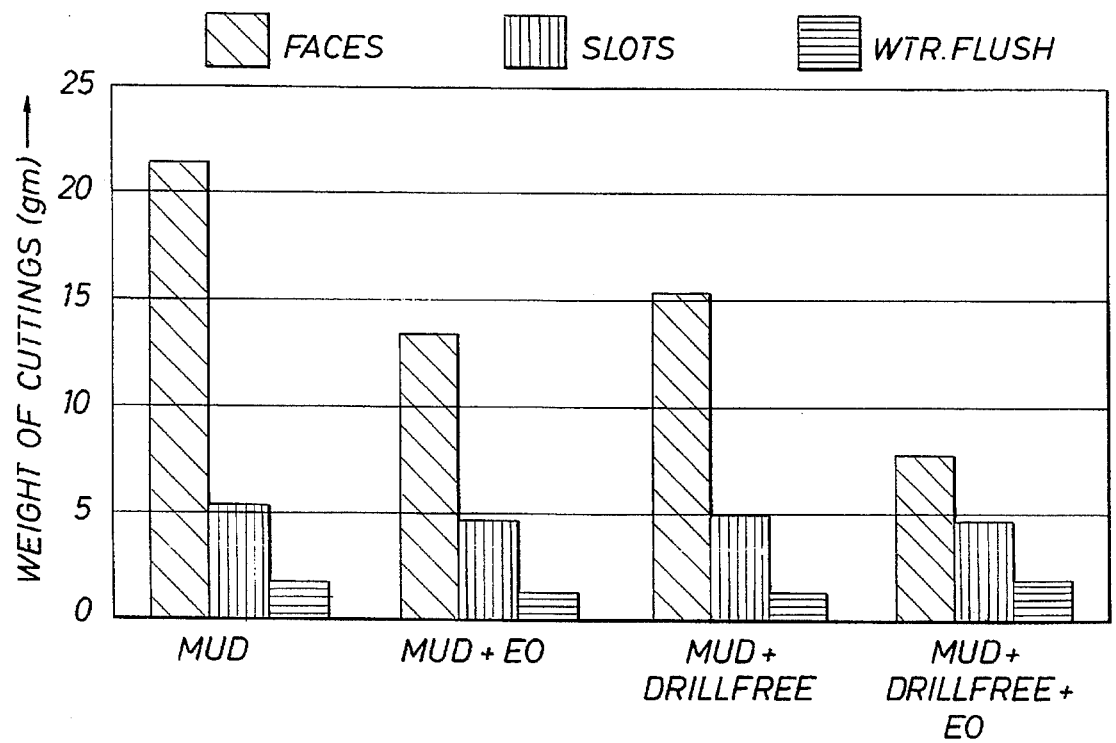

FIG. 12 shows test results that indicate improvement (reduction) of bit-balling amount due to DRILLFREE additive.

DESCRIPTION OF THE PREFERRED EMBODIMENTS

The test procedure of the invention involves preparation of a sample such as a rock sample which may be shale, sandstone, etc., and a test fluid such as a drilling fluid that is well known to the art, mounting the sample in the test cell and adding the test fluid which is circulated through the cell during the duration of the experiment; rotating the bob which has been described earlier above, against the rock sample under a specified load for the specified duration of the experiment, draining the test fluid, removing the cell and then removing the bob and weighing the bob with the stuck/adhered rock cuttings to it and recording the weight, then carefully removing the stuck cuttings from the faces of the bob alone and weighing for a second time and record the second weight and then carefully remove the stuck cuttings from the slots of the bob and then weighing for a third time and record the third weight; then clean bob of all remaining cuttings from both faces and slots with water and then weigh for fourth time the dry bob alone and record fourth weight; the difference between first weight and second weight providing the amount of balling on the faces alone; the difference between second weight and third weight providing the amount of balling in slots; the difference between third weight and fourth weight providing the amount of stuck cuttings remaining on both faces and slots combined, provides the amount of balling on the faces, slots and remaining balled cuttings, respectively.

Figure 1:
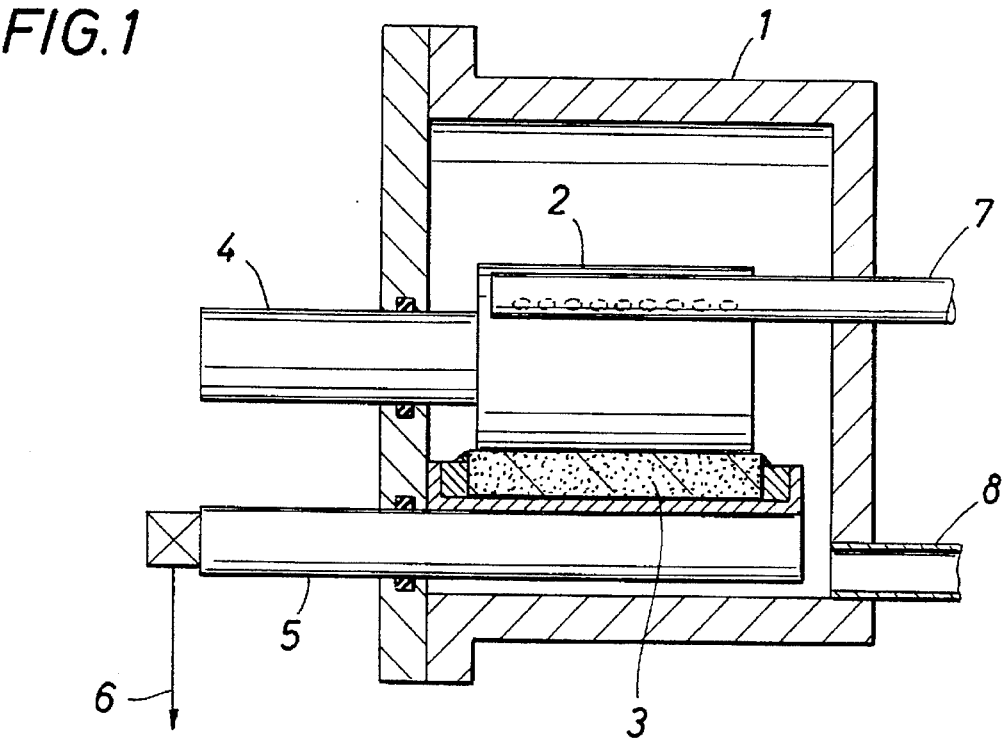
FIG. 1 is the cross-section of the apparatus of the invention.
Figure 2:
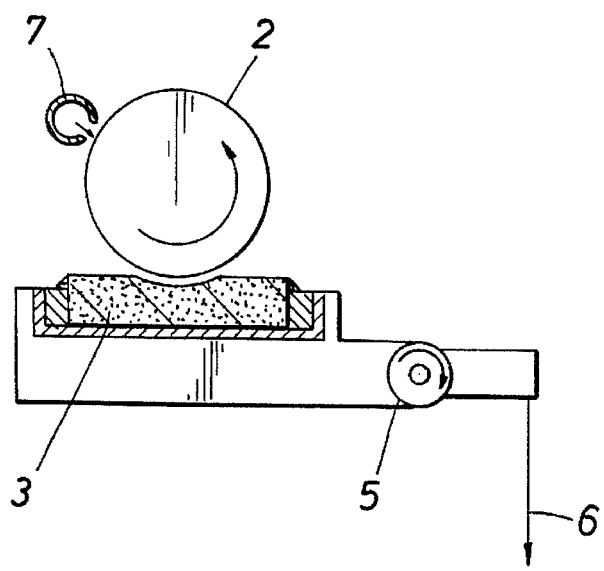
FIG. 2 is a front view of the apparatus of the invention.

As shown in FIGS. 1 and 2 a test cell housing 1 is provided which encloses a bob or cutter 2 and a rock sample 3. The bob is rotated by a main shaft or spindle 4 which extends through the wall of the test cell housing. The rock sample 3 is forced against the bob 2 by load shaft 5, which is under pressure from a load 6. Fluid inlet 7 and fluid outlet 8 are provided for circulating a test fluid such as a drill fluid through the test cell housing and into contact with the bob and the rock sample.

As explained above, after the apparatus has been run for a period of time with the bob rotated against the rock sample, the device is then shut down, the circulation of the fluid is stopped and the fluid drained from the test chamber, the bob is removed from the main shaft/spindle and weighed. After the cuttings from the faces and slots have been removed step by step and weighted between each removal operation of the balled up cuttings, the differences between each previous weighing and the subsequent weighing indicates the amount of bit-balling occurring for the bit-like bob under the particular set of controlled experimental parameters used for the particular experiment.

The following tests were conducted to study the phenomenon of bit/stabilizer balling utilizing the said test apparatus and bob.

EXAMPLE 1

This test was conducted to determine which of the above listed bob designs (1 through 6) would be heavily balled with cuttings and which would be cleaner.

Bit/stabilizer balling test was conducted using each of the six designs using identical pieces of Pierre II shale as rock specimen in fresh water as the drilling fluid for the same duration of time. The amount of balled cuttings were measured at the end of the experiment for each bob on the faces, slots and after flushing with water. The test parameters are as below.

| | |
|---|---|
| Weight-on-bob | 50 lb |
| RPM | 75 |
| Fluid | Fresh Water |
| Duration | 120 sec |
| Rock | Pierre II Shale |

SUMMARY OF TEST RESULTS

The results are illustrated in FIG. 9. The test results provided excellent results. The amount of balled up cuttings on the faces varied from 2 gm for Design 4 to about 25 gm for Design 5. The amount of balling for Design 6 the optimized design was about 22 gm. The balled up shale cuttings were extremely sticky and difficult to remove. The balling for the other Designs 1, 2 and 3 was about 14 gm, 2 gm and 12 gm, respectively. For Design 2 the amount of balling in the slots was observed to be more than on the faces.

EXAMPLE 2

This test was conducted to examine consistency and repeatability of balled experimental data. It was found that the bob which provided the most consistent and repeatable data was Design 6. After a number of tests have been run on the this bob, at various test parameters and durations at periodic intervals the 'control' test was run with the following test conditions.

| | |
|---|---|
| Weight-on-bob | 50 lb |
| RPM | 75 |
| Fluid | Fresh Water |
| Duration | 120 sec |
| Rock | Pierre II Shale |

SUMMARY OF TEST RESULTS

The test result is shown in FIG. 10. The plot of Number of Tests versus Weight of Stuck Cuttings shows excellent repeatability of the balled up amount for identical experimental conditions. The amount of balled up cuttings on the faces remains around an average value of about 21 gm even after about 70 tests with the bob under different conditions of weight and rpm. The same trend with the amount of stuck cuttings in the slots is noticed, remaining constant at about 5 gm.

EXAMPLE 3

This test was conducted to examine the effectiveness of the process of electro-osmosis in the prevention of bit/stabilizer balling. Here the rock sample was held in an insulated rock holder and maintained at a positive potential with respect to the bob at +10 VDC. The bob was connected to the negative terminal of the 10 VDC power supply making it the cathode. The test parameters were as below.

| | |
|---|---|
| Weight-on-bob | 50 lb |
| RPM | 75 |
| Fluid | Fresh Water |
| Duration | 120 sec |
| Rock | Pierre II Shale |
| Voltage | 10VDC |

SUMMARY OF TEST RESULTS

The test results are shown in FIG. 11. The figure shows the amount of stuck balled cuttings of Pierre II shale rock on the faces, slots and after cleaning with water for both the conditions viz. when no electo-osmosis was applied and when a 10 VDC potential was applied making the bob the cathode.

It is clearly seen that the amount of balling on the faces is reduced from 20 gm to about 7 gm, a reduction of about 65%. The amount of balling in the slots is reduced to by about 20% through this novel process for prevention of bit/stabilizer balling called electro-osmosis.

EXAMPLE 4

This series of four tests were conducted to examine the effectiveness of a particular drilling additive to the drilling fluid, as well as the effect of electro-osmosis in the prevention of bit-balling. The tests were:

(i) Control, which involved conducting balling test in the specified drilling fluid without any additives or electro-osmosis.

(ii) Additive was the balling test with the drilling fluid containing additive DRILLFREE by MI Drilling Fluids (75 lb/bbl).

(iii) Electro-Osmosis (EO), which consisted of the test with maintaining the bob at a negative electrical potential with respect to the rock sample maintained at 10 VDC in the drilling fluid containing no DRILLFREE.

(iv) Mud+EO+DRILLFREE consisted of the test for balling of the drilling fluid containing the additive DRILLFREE of 0.75/bbl concentration combined with electro-osmosis at 10 VDC maintaining the bob at a negative potential of 10 VDC with respect to the rock sample. The test conditions are shown below:

| | |
|---|---|
| Weight-on-bob | 50 lb |
| RPM | 75 |
| Duration | 120 sec |
| Voltage | 10VDC |
| Fluid | Frsh Water |
| Rock | Pierre II Shale |
| Additive | DRILLFREE |

The test results are shown in FIG. 12.

From the results it is seen that DRILLFREE reduces the amount of bit-balling from 22 gm (Control) to about 15 gm, a reduction of about 32%. Electro-osmosis alone reduces the amount of balling on the faces by about 41%. When electro-osmosis and the fluid additive both are used, the total reduction in balling is from 22 gm to about 7 gm; 68%. These test results indicate that the amount of bit/stabilizer balling can be measured and quantified.

What is claimed is:

1. A laboratory process for determining the likelihood and/or extent of stabilizer balling occurring in the presence of a specified formation material through which a borehole would be drilled and a specified drilling which would be used to drill the borehole, thereby providing an indication of the actual likelihood and/or extent of bit/stabilizer balling to be expected during actual borehole drilling in the field, comprising:

providing a sample of the specified formation material or a similar substitute to be enclosed within a fluid-pressurized test chamber:

providing a sample of the specified drilling fluid to be enclosed within a fluid-pressurized test chamber or a similar substitute fluid;

providing one or many specially designed bob with teeth, faces and slots machined in its surface simulating the drill bit or stabilizer to be used for drilling the well or a similar substitute bob;

enclosing the bob and the formation material in the drilling fluid that fills said test chamber;

forcing the bob against the formation material with the application of a specified predetermined load;

rotating the bob for a selected duration of time; and subsequently removing and weighing the bob to determine how much formation material is adhering to the bob.

2. An apparatus for determining bit-balling tendencies of a drill bit used to drill into a specified rock sample comprising:

a variety of specially designed bobs simulating a drill bit;

a holder for a rock sample;

a chamber enclosing the bob holder and rock sample;

a fluid inlet and a fluid outlet to the chamber for passing drilling fluid in contact with the bob and the rock sample;

means for rotating the bob while in contact with said rock sample under the application of a specified predetermined load;

means for weighing the bob before and after said rotation;

means for measuring and recording the rotary torque generated at the interface of the bob and the rock sample;

means for measuring and recording the rotary speed at which the bob is rotated when in contact with the rock and also when not in contact with the rock sample.

* * * * *